United States Patent [19]

Löhn

[11] Patent Number: 4,642,051
[45] Date of Patent: Feb. 10, 1987

[54] DENTAL HANDPIECE

[75] Inventor: Gerd Löhn, Biberach, Fed. Rep. of Germany

[73] Assignee: Kaltenbach & Voigt GmbH & Co., Biberach, Fed. Rep. of Germany

[21] Appl. No.: 757,609

[22] Filed: Jul. 22, 1985

[30] Foreign Application Priority Data

Sep. 14, 1984 [DE] Fed. Rep. of Germany ....... 3433876

[51] Int. Cl.$^4$ ............................................. A61C 1/02
[52] U.S. Cl. ................................... 433/100; 433/126
[58] Field of Search ................. 433/100, 126, 132, 120

[56] References Cited

U.S. PATENT DOCUMENTS

| 3,574,374 | 4/1971 | Keller | 433/126 |
| 4,182,038 | 1/1980 | Fleer | 433/126 |
| 4,278,427 | 7/1981 | Lingenhole et al. | 433/100 |
| 4,403,958 | 9/1983 | Lohn | 433/126 |

FOREIGN PATENT DOCUMENTS 2311496 9/1974 Fed. Rep. of Germany ...... 433/126
2047348 11/1980 United Kingdom ................ 433/100

Primary Examiner—John J. Wilson
Attorney, Agent, or Firm—Scully, Scott, Murphy & Presser

[57] ABSTRACT

A dental handpiece, consisting of a gripping sleeve part with a built-in air motor for the drive of a treating implement which is supported within the gripping sleeve part. The gripping sleeve part has a detachable connecting member associated therewith; and the air motor has a control device possessing a handgrip associated therewith for changing the direction of rotation of the air motor; and wherein the connecting member is further provided with two passageways having outlet orifices connectable with the air motor for, respectively, the infeed of driving air and the discharge of exhaust air. For collective gripping sleeve parts which are brought into exchangeable engagement with the connecting member, it is necessary to provide only a single control device for changing the direction of rotation, which results in a simple mounting of bearing support for the gripping sleeve parts.

4 Claims, 10 Drawing Figures

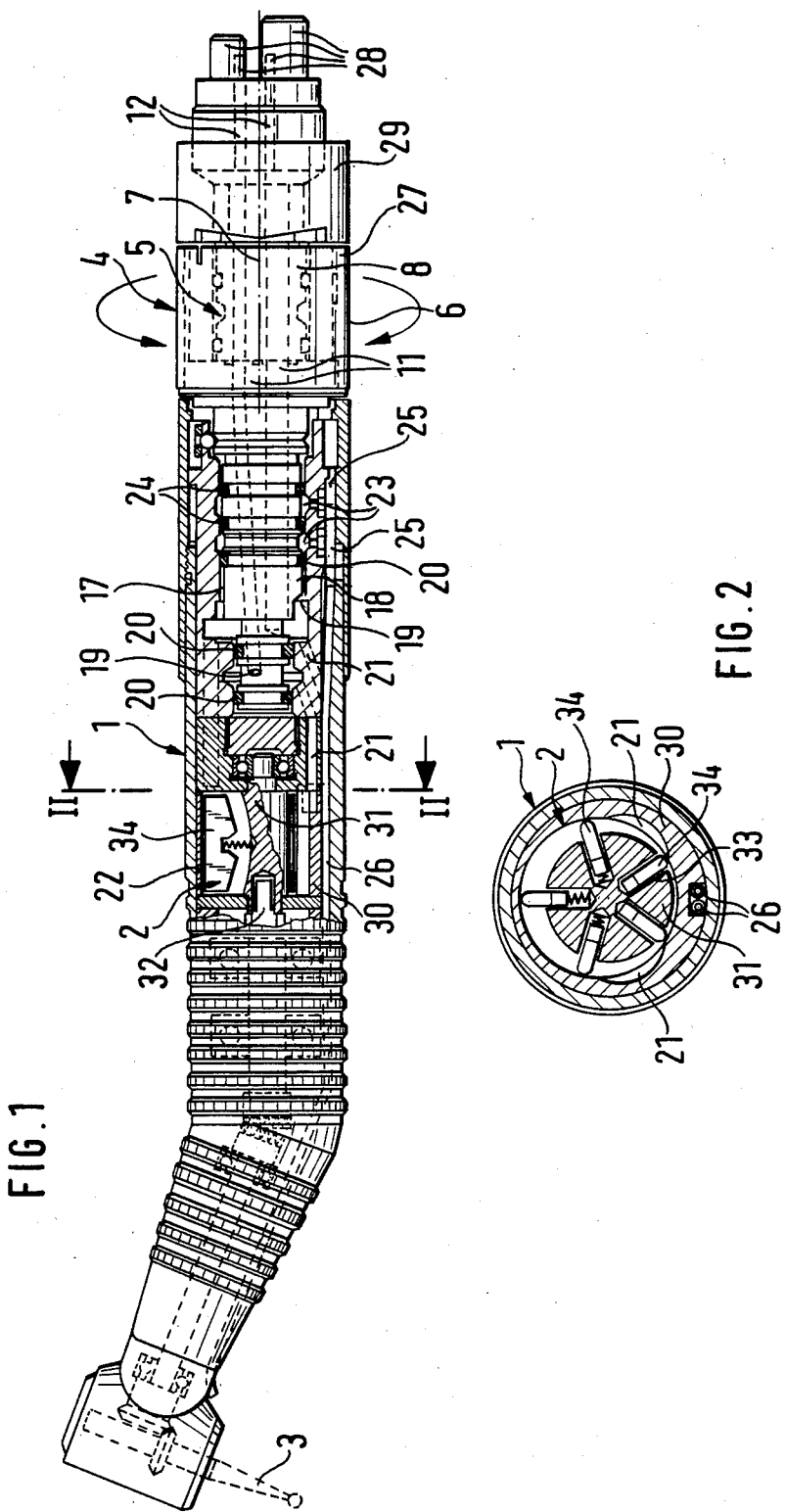

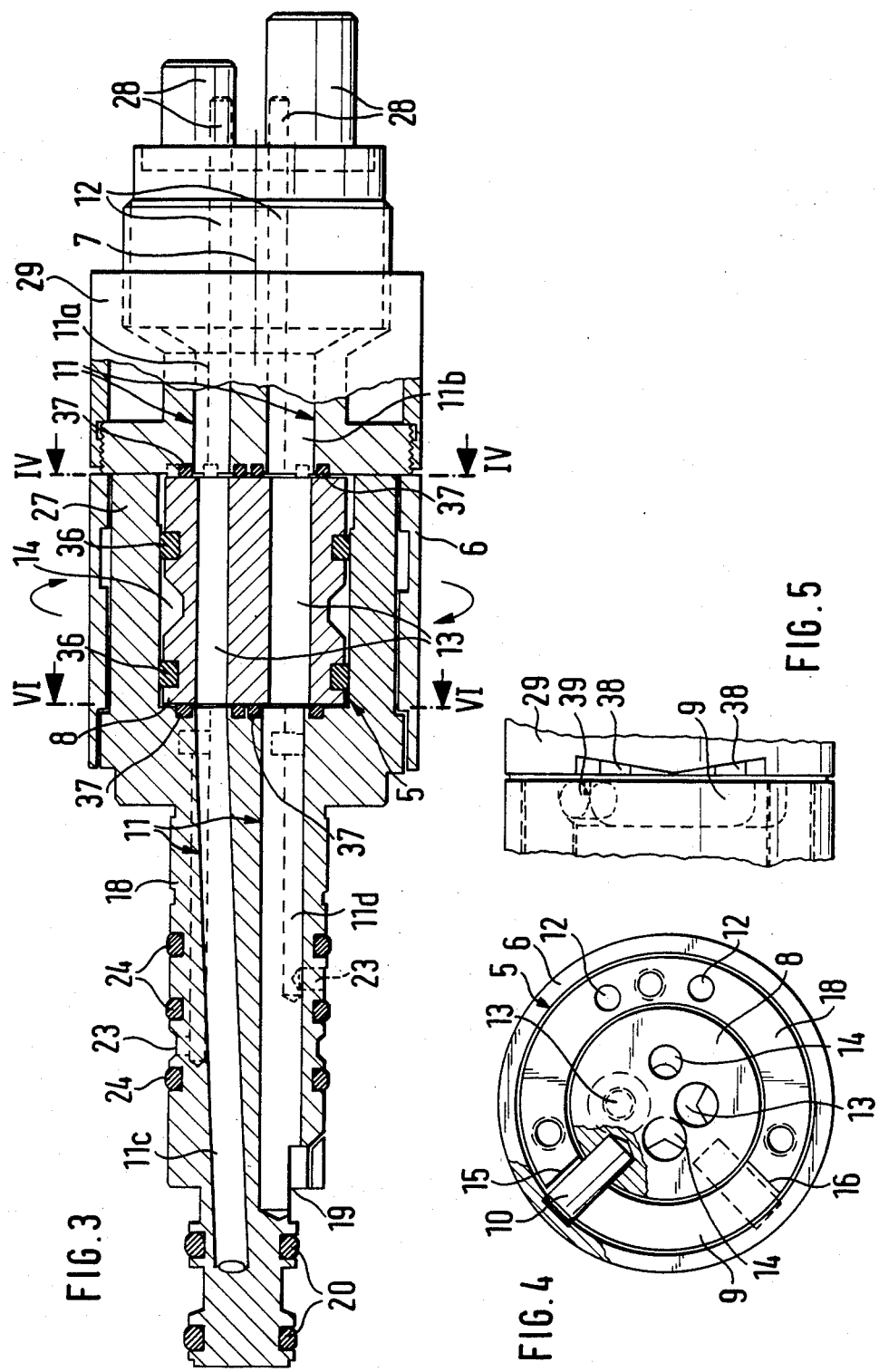

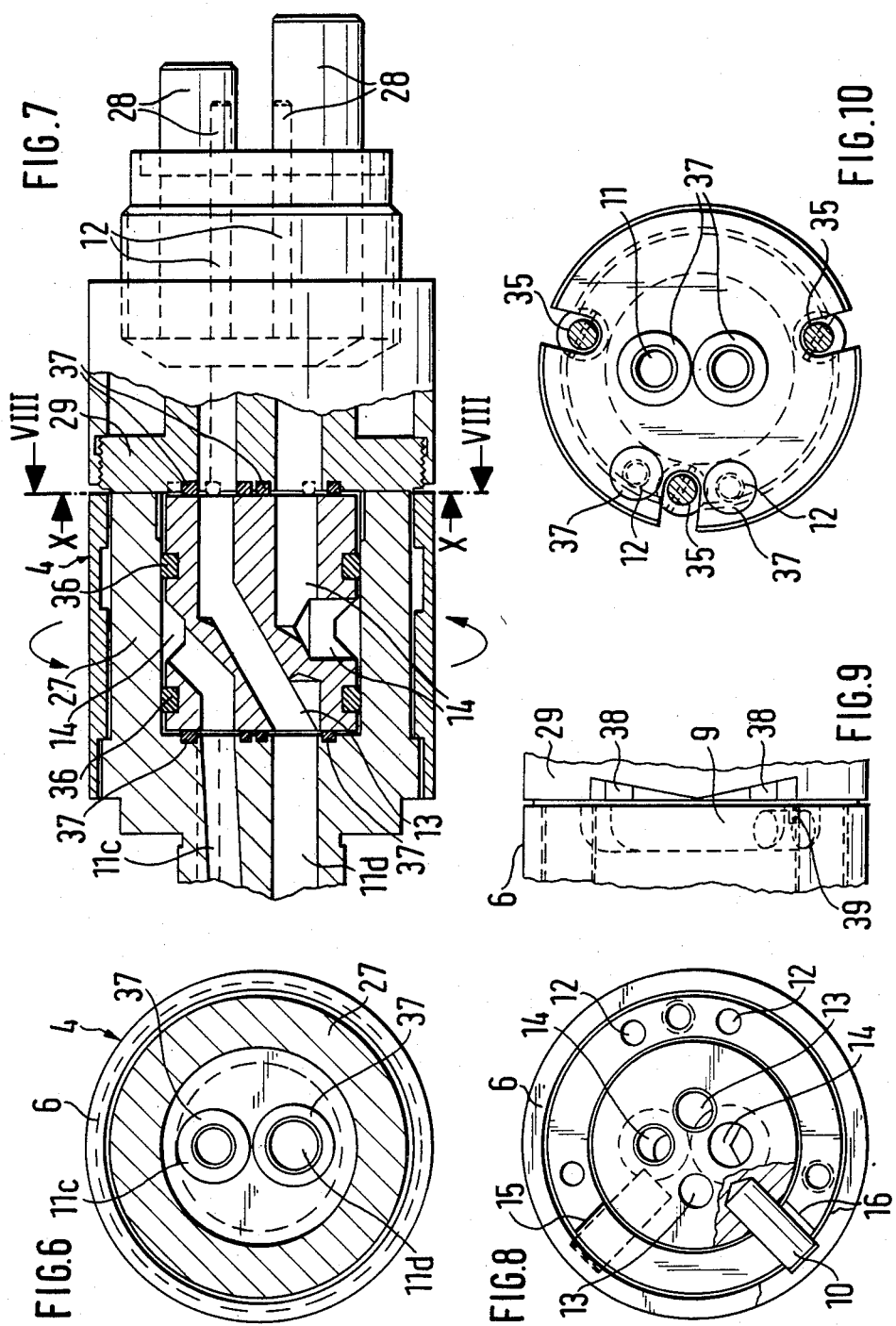

DENTAL HANDPIECE

BACKGROUND OF THE INVENTION

1. Field of the Invention

The present invention relates to a dental handpiece, consisting of a gripping sleeve part with a built-in air motor for the drive of a treating implement which is supported within the gripping sleeve part, wherein the gripping sleeve part has a detachable connecting member associated therewith; and the air motor has a control device possessing a handgrip associated therewith for changing the direction of rotation of the air motor; and wherein the connecting member is further provided with two passageways having outlet orifices connectable with the air motor for, respectively, the infeed of driving air and the discharge of exhaust air.

2. Discussion of the Prior Art

A dental handpiece of that type has become known from the disclosure of German Laid-Open Patent Application No. 30 09 337. In this known handpiece, the control device is arranged within the gripping sleeve part. It is a frequent occurrence that due to reasons necessitated by the operation or the treatment, the air motor-gripping sleeve part which is connected with the connecting member so as to be easily detachable; for example, a gripping sleeve part which is adapted for the drilling out of tooth cavities, is to be exchanged for a differently constructed gripping sleeve part; for example, which is adapted for the treating of a tooth root canal. In order to, in every instance, ensure that the treating person can change the direction of rotation of the air motor; in effect, reverse from clockwise rotation to counterclockwise rotation, it is necessary that each gripping sleeve part which is connectable with the connecting member must be provided with a control device for changing the direction of rotation. As a result, there is obtained a complex mounting or bearing support.

SUMMARY OF THE INVENTION

The present invention, as can be ascertained from the following detailed description, has as its object the provision of a dental handpiece of the above-mentioned type, in which the demands on the arrangement of the control device for effecting the change in the direction of rotation is reduced in view of the exchange of the gripping sleeve part.

The advantages which can be achieved by means of the present invention can be essentially ascertained in that for collective gripping sleeve parts which are brought into exchangeable engagement with the connecting member, it is necessary to provide only a single control device for changing the direction of rotation, which results in a simple mounting or bearing support for the gripping sleeve parts.

BRIEF DESCRIPTION OF THE DRAWINGS

Further advantageous embodiments and features of the invention can be readily ascertained from the following detailed description thereof, taken in conjunction with the accompanying drawings illustrating exemplary embodiments; in which:

FIG. 1 illustrates a side view, partly in section, of a dental handpiece;

FIG. 2 illustrates a sectional view taken along line II—II in FIG. 1;

FIG. 3 illustrates the connecting member of the handpiece of FIG. 1 with the control device in an end rotational position effecting the clockwise rotation of the air motor, shown in section and on an enlarged scale;

FIG. 4 illustrates a sectional view taken along line IV—IV in FIG. 3;

FIG. 5 illustrates a side view of the embodiment of FIG. 4;

FIG. 6 illustrates a sectional view taken along line VI—VI in FIG. 3;

FIG. 7 illustrates the connecting member of FIG. 3 with an omitted complete extension with the control device in an end rotational position effecting the counterclockwise rotation of the air motor;

FIG. 8 illustrates a sectional view taken along line VIII—VIII in FIG. 7;

FIG. 9 illustrates the embodiment of FIG. 8 in a side view; and

FIG. 10 illustrates a sectional view taken along line X—X in FIG. 7.

DETAILED DESCRIPTION

The dental handpiece consists of a gripping sleeve part 1 with a built-in air motor 2 for the drive of a treating implement 3 which is supported within the gripping sleeve part. Associated with the gripping sleeve part is an easily detachable connecting member 4 for the connection of a supply hose (not shown), whereas the air motor 2 has associated therewith a control device 5 possessing a handgrip 6 for implementing the change; in essence, for reversing the direction of rotation of the air motor 2. The connecting member 4 is provided with two or more passageways 11 connected with infeed conduits in the supply hose, which are connectable with the air motor 2 through outlet orifices 19 for the infeed of driving air and for the discharge of exhaust air.

The air motor 2, which can also be designated as a compressed-air motor, can be constructed, for example, pursuant to German OS No. 19 41 159 as a turbine with a rotor provided with impeller blades; or pursuant to German AS No. 12 32 789 as a piston motor with a rotor having cylinders for the pistons, for instance, in the form of balls; or pursuant to German OS No. 23 04 666 as a vaned motor having a rotor which is provided with slots for radially movable vanes. The illustrated air motor is constructed as a vaned motor and, pursuant to FIGS. 1 and 2, consists of a housing 30 forming the stator, within which there is arranged a rotatably supported rotor 31 which can be placed into rotation through driving compressed air which is introduced into the housing by means of one of the passageways 11; which rotor incorporates a shaft 32 connectable with the implement 3, for example, a dental drill. In elongated slots 33 of the rotor 31, vanes 34 are radially movably supported.

The control device with is associated with the passageways 11 is arranged within the connecting member 4.

The control device 5 consists of a rotary slide valve 8 which is supported within the connecting member 4, and which possesses a handgrip 6 which is rotatable about the axis 7 of the connecting member. In this instance, the handgrip 6 is formed by a turn ring which externally encompasses the connecting member 4, and which is connected with the rotary slide valve 8 by means of a follower 10 projecting through a radial guide slot 9 provided in the connecting member 4.

As can be further ascertained from the drawing, the construction of the handpiece is such that the passageways 11 are interrupted over the axial length of the rotary slide valve 8, with the formation of partial passageways 11a, 11b remote from the gripping sleeve, and partial passageways 11c, 11d towards the gripping sleeve part which possess the outlet orifices 19; and the rotary slide valve 8 is located in the region of the interruption, whereby the rotary slide valve includes two paired connecting passageways 13, 14 of which, in the one rotational end position of the rotary slide valve 8, the one pair 13 of the partial passageway 11a remote from the gripping sleeve part conducting the driving air connects with the one partial passageway 11c towards the gripping sleeve part, as well as the partial passageway 11b remote from the gripping sleeve part which conducts the exhaust air with the other partial passageway 11d towards the gripping sleeve part; and for reversing the direction of rotation of the air motor 2 in the other rotational end position of the rotary slide valve 8, the other pair 14 of the partial passageway 11a remote from the gripping sleeve part connects with the other partial passageway 11d towards the gripping sleeve part, as well as the partial passageway 11b remote from the gripping sleeve part with the partial passageway 11c towards the gripping sleeve part.

The radial guide slot 9 in the connecting member 4 possesses stops 15, 16 at its ends, whose location corresponds to the two rotational end positions of the rotary slide valve.

The partial passageways 11c, 11d towards the gripping sleeve part are arranged in a trunnion-shaped extension 18 of the connecting member 4 which is detachably insertable into an axial receiving opening 17 in the gripping sleeve part 1. In particular from FIG. 3 can there be ascertained that the extension 18 includes annular channels sealed by sealing rings 20 coming into contact against the inner wall of the receiving opening 17 of the gripping sleeve part, into which there connect the outlet orifices 19 of the partial passageways 11c, 11d towards the gripping sleeve part, whereby the annular channels are connected through connecting channels 21 in the gripping sleeve part 1 with the operating chamber 22 of the air motor 2. The extension 18 possesses a latching arrangement in which it is maintained in a preset reference position in which it is inserted into the receiving opening 17, and in which the annular channels are sealed. Suitably, the above-mentioned sealing rings 20 assume the task of the latching arrangement. Hereby, there can be arranged further inlet passageways 12 in the connecting member which reach into the extension 18, which connect from the extension 18 by means of outlet orifices 23 into annular spaces which are sealed by sealing rings 24 coming into engagement with the inner wall of the receiving opening 17 of the gripping sleeve part 1, wherein the last-mentioned annular spaces possess further conducting passageways 26 of the gripping sleeve part 1 having inlet openings 25, and leading to the area of the implement 3.

As illustrated in the drawing, the upper passageway 11 which during the clockwise rotation of the air motor 2, serves for the infeed of driving air, possesses a smaller cross-section than the lower passageway 11 which, in this instance, serves for the discharge of exhaust air.

For reasons of an easier servicing or supplemental equipping, pursuant to FIGS. 3 and 10 the control device 5 is arranged in an attaching member 27 of the connecting member 4, which includes the projecting 18, whereby the attaching member 27 is detachably connected with the aid of screws 35 with a main body 29 of the connecting member 4 possessing media connections 28. Hereby, the sealing of the passageways 11 is effected through ring seals 37.

For the remainder, the rotary slide valve 8, depending upon circumstances, is sealed in view of the ring-shaped section of the connecting passageway 14, with the aid of sealing rings 36 relative to the connector member 4.

As can be ascertained from FIGS. 5 and 9, arranged on the stationary portion of the connector member 4; in effect, on the main body 29, is a scale 38 for, respectively, the clockwise rotation and the counterclockwise rotation of the air motor 2, and an indicator 39 on the handgrip 6, the latter of which is formed as a turn ring.

What is claimed is:

1. A dental handpiece, a gripping sleeve part having a built-in air motor for the drive of a treating implement which is supported in the gripping sleeve part; a detachable connecting member being associated with the gripping sleeve part; a control device possessing a handgrip for changing the direction of rotation of the air motor being associated with said air motor; said control device including a rotary slide valve and said handgrip being an external turn ring including a follower projecting through a radial guide slot in said connecting member for connection with the rotary slide valve; said connecting member including two passageways connectable with the air motor through outlet orifices for, respectively, the infeed of driving air and for the discharge of exhaust air; said radial guide slot including stops at the ends thereof wherein the positions of said stops corresponds to the two rotational end positions of the rotary slide valve, the passageways towards the gripping sleeve part being arranged in a trunnion-shaped extension of the connecting member which is detachably insertable into the axial receiving opening of the gripping sleeve part, the extension including annular channels; sealing rings for saling said channels through contacting the inner wall of the receiving opening of the gripping sleeve part, the outlet orifices of the partial passageways towards the gripping sleeve part communicating with said channels whereby said annular channels connect through connecting passageways in the gripping sleeve part with the work chamber of said air motor; said control device being arranged centrally and coaxially in the core of the connecting member, said passageways being interrupted over the axial length of the rotary slide valve, with the formation of partial passageways remote from the gripping sleeve, and partial passageways towards the gripping sleeve part which possess the outlet orifices; the rotary slide valve including two paired connecting passageways of which, in the one rotational end position of the rotary slide valve, the one pair of the partial passageway remote from the gripping sleeve part driving air connecting with the one partial passageway towards the gripping sleeve part, as well as connecting the partial passageway remote from the gripping sleeve part which conducts the exhaust air with the other partial passageway towards the gripping sleeve part; and for reversing the direction of rotation of the air motor in the other rotational end position of the rotary slide valve, the other pair of the partial passageway remote from the gripping sleeve part connecting with the other partial passageway towards the gripping sleeve part, as well as connecting the partial passageway remote from the gripping sleeve part with the partial passageway towards the gripping sleeve part.

2. A handpiece as claimed in claim 1, wherein further media inlet passageways extending into the projection are arranged within the connector member, said passageway connecting from the extension through outlet orifices into annular spaces, sealing rings contacting the inner wall of the receiving opening of the gripping sleeve part for sealing said annular spaces, said passageways including extension passageways to the region of the implement and including inlet openings.

3. A handpiece as claimed in claim 1, wherein the passageway serving for the infeed of driving air during the clockwise rotation of the air motor has a smaller cross-section than the passageway serving for the discharge of exhaust air.

4. A handpiece as claimed in claim 1, wherein the control device is arranged in an extension member of the connector member, said extension member being detachably connected with a main body of the connecting member possessing media connections.

* * * * *